United States Patent [19]
Bara et al.

[11] Patent Number: 5,902,592
[45] Date of Patent: May 11, 1999

[54] COSMETIC COMPOSITION COMPRISING CYCLOPENTADIMETHYLSILOXANE AND CYCLOHEXADIMETHYLSILOXANE IN FATTY PHASE

[75] Inventors: Isabelle Bara, Paris; Nadia Terren, Chevilly Larue; Jacques Michelet, Champlan, all of France

[73] Assignee: L'Oreal, Paris, France

[21] Appl. No.: 08/872,181

[22] Filed: Jun. 10, 1997

Related U.S. Application Data

[63] Continuation of application No. 08/539,743, Oct. 5, 1995, abandoned.

[30] Foreign Application Priority Data

Oct. 10, 1994 [FR] France ................................. 94 12071

[51] Int. Cl.$^6$ .......................... A61K 7/027; A61K 7/031; A61K 7/032; A61K 7/48
[52] U.S. Cl. ............................. 424/401; 424/63; 424/64; 424/501; 424/502; 524/588
[58] Field of Search ............... 424/63, 64, 401, 424/501, 502; 524/588

[56] References Cited

U.S. PATENT DOCUMENTS

| | | | |
|---|---|---|---|
| 4,280,994 | 7/1981 | Turney | 424/68 |
| 4,720,353 | 1/1988 | Bell | 252/309 |
| 4,780,145 | 10/1988 | Mori et al. | 106/206 |
| 4,917,891 | 4/1990 | Kaufmann et al. | 424/401 |
| 5,292,530 | 3/1994 | McCrea et al. | 424/68 |
| 5,326,387 | 7/1994 | Faber et al. | 106/3 |
| 5,384,115 | 1/1995 | Bissett et al. | 424/64 |
| 5,486,566 | 1/1996 | Katsoulis | 424/65 |

FOREIGN PATENT DOCUMENTS

| | | |
|---|---|---|
| 610 014 | 8/1994 | European Pat. Off. . |
| 613 679 | 9/1994 | European Pat. Off. . |

OTHER PUBLICATIONS

Chemical Abstracts, vol. 115, No. 16, Oct. 21, 1991; Abstract No. 166398; N. Watanabe, Water–in–oil Cosmetic Emulsions Containing Cyclic Silicones.

*Primary Examiner*—Robert E. Sellers
*Attorney, Agent, or Firm*—Finnegan, Henderson, Farabow, Garrett & Dunner, L.L.P.

[57] ABSTRACT

A cosmetic composition formulated as an oil-in-water or water-in-oil emulsion, or a paste or powder contains a fatty phase comprising volatile and cyclic silicone oils of from 2–18 weight % of cyclopentadimethylsiloxane and 2–18 weight % of cyclopentadimethylsiloxane, the weight percentages based on the total weight of the composition.

18 Claims, No Drawings

COSMETIC COMPOSITION COMPRISING CYCLOPENTADIMETHYLSILOXANE AND CYCLOHEXADIMETHYLSILOXANE IN FATTY PHASE

This is a continuation of application Ser. No. 08/539,743, filed Oct. 5, 1995, now abandoned.

The present invention relates to a cosmetic composition which can be provided in the form of an oil-in-water or water-in-oil emulsion, or alternatively in the form of a paste or of a powder, comprising silicone compounds, and inter alia silicone oils.

Make-up cosmetic compositions, such as foundation creams, are known which are provided in the form of a water-in-oil emulsion in which the oil phase, or fatty phase, is composed mainly of silicone fatty substances.

After application of such a composition, the water evaporates and the silicone compounds remain in contact with the skin, resulting in make-up which can be water-resistant. However, the application of such compositions has the disadvantage of leaving the skin with an oily appearance and of resulting in a greasy effect to the touch. The result obtained after application is not truly natural; the make-up shines or becomes shiny.

The aim of the present invention is to provide a cosmetic composition which results in a make-up which is pleasant to apply and which remains non-shiny with time, while avoiding the feeling of greasiness to the touch.

A subject of the present invention is therefore a cosmetic composition comprising, in a fatty phase, the combination of at least two volatile and cyclic silicone oils, cyclopentadimethylsiloxane and cyclohexadimethylsiloxane.

Another subject of the invention is the use, in a cosmetic composition comprising a fatty phase, of the combination of at least two volatile and cyclic silicone oils, cyclopentadimethylsiloxane and cyclohexadimethylsiloxane.

Thus, when the composition according to the invention is used, the volatile silicone oils evaporate on contact with the skin and make it possible to obtain make-up which is not shiny and which remains matte with time. Moreover, the make-up obtained is not oily to the touch.

An advantage of the composition according to the invention is that it is easy to apply, spreading easily and uniformly.

Another advantage is that of having a light and fluid texture which is soft to the touch.

Another advantage is that of making it possible to obtain a make-up with a natural color, with good covering power and good hold.

The composition according to the invention can be provided in the form of an oil-in-water, water-in-oil or multiple emulsion, in the form of a stick, in the form of a paste, which may or may not be anhydrous, or alternatively in the form of a compact or cast powder.

The composition according to the invention therefore comprises, in a fatty phase, at least cyclopentadimethylsiloxane oil and cyclohexadimethylsiloxane oil.

In fact, it was observed that, in the compositions thus obtained, the cyclopentadimethylsiloxane contributes to providing for ease of make-up, by supplying slip to the composition and by making it easier for the latter to be spread over the skin. This oil then rapidly evaporates after application. Cyclohexadimethylsiloxane, which is slower to evaporate, contributes to the comfort of the make-up and makes it possible to keep the skin supple, while preventing tightness and a dry feeling.

Preferably, the composition comprises a mixture of cyclopentadimethylsiloxane in an amount of 2–18 weight % with respect to the total weight of the composition and of cyclohexadimethylsiloxane in an amount of 2–18 weight %.

The composition can optionally comprise other volatile oils. In the present description, volatile oil is understood to mean any oil capable of evaporating on contact with the skin. Use is preferably made of oils whose flash point is sufficiently high to make it possible to use these oils in formulations and sufficiently low to obtain the desired evanescent effect. Oils whose flash point is of the order of 50–100° C. are preferably employed.

Oils having different degrees of volatility are preferably employed, so as to retain appropriate cosmetic qualities in the final composition. Mention may in particular be made of cyclic or linear silicone oils, such as cyclotetradimethylsiloxane or X2-1731 from Dow Corning, and/or organic oils, in particular paraffin oils such as the Isopars.

The composition according to the invention preferably comprises 4–20 weight % of volatile oils with respect to the total weight of the composition.

The composition can comprise, in addition to the volatile oils, constituents commonly used in the cosmetics field.

Mention may be made, among the latter, of silicone fatty substances, such as non-volatile silicone oils, silicone gums or silicone waxes, and of non-silicone fatty substances, such as vegetable, mineral, organic and/or synthetic oils or waxes. The non-volatile silicone oils which can be used in the composition according to the invention can be oils of low viscosity, such as linear polysiloxanes, whose degree of polymerization is preferably from 3 to 2000 approximately.

The oil can generally be present in an amount of 0–15 weight % in the final composition, preferably 10–13%. Mention may be made, for example, of:

polydimethylsiloxanes (PDMS) with a viscosity of less than 100 mPa·a and preferably of less than 10 mPa·s alkyldimethicones corresponding to the formula:

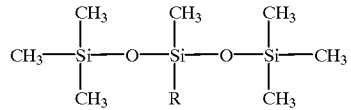

in which R represents the radical $C_nH_{2n+1}$, with n=1 to 8, polyphenylmethylsiloxanes. Mention may be made, for example, of Silbione oil 70-047V from Rhône-Poulenc, 200 oil from Dow Corning or polycetylmethylsiloxane oil from Goldschmidt.

The silicone gums which can be used in the composition according to the invention can be polysiloxanes of high molecular mass, of the order of 200,000 to 1,500,000, preferably 200,000 to 1,000,000.

They can be used alone or as a mixture with a solvent such as a polydimethylsiloxane or polyphenylsiloxane oil.

The gum can generally be present in an amount of 0–1 weight % of active material in the final composition, preferably in the proportion of 0.1–0.5%.

The silicone gum can correspond to the formula:

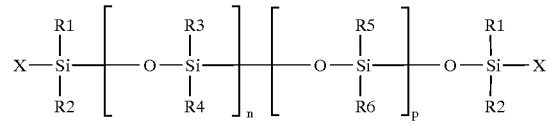

in which:

R1, R2, R5 and R6 each individually represents an alkyl radical having 1 to 6 carbon atoms, R3 and R4 each individually represents an alkyl radical having from 1 to 6 carbon atoms or an aryl radical, X is an alkyl radical having from 1 to 6 carbon atoms, a hydroxyl radical or a vinyl radical, n and p are chosen so as to confer a viscosity greater than 100,000 mPa·s, preferably greater than 500,000 mPa·s, on the silicone gum.

Generally, n and p can take values from 0 to 5000, preferably from 0 to 3000.

Mention may be made, as silicone gum which can be used according to the invention, of those in which:

the substituents R1 to R6 and X represent a methyl group, p=0 and n=2700, like that sold under the name SE30 by the company General Electric, the substituents R1 to R6 and X represent a methyl group, p=0 and n=2300, like that sold under the name AK 500000 by the company Wacker, the substituents R1 to R6 represent a methyl group, the substituent X represents a hydroxyl group, p=0 and n=2700, as a 13% solution in cyclopentasiloxane, like that sold under the name Q2-1401 by the company Dow Corning, the substituents R1 to R6 represent a methyl group, the substituent X represents a hydroxyl group, p=0 and n=2700, as a 13% solution in polydimethylsiloxane, like that sold under the name Q2-1403 by the company Dow Corning, the substituents R1, R2, R5, R6 and X represent a methyl group and the substituents R3 and R4 represent an aryl group, such that the molecular weight of the compound is 600,000, like that sold under the name 761 of the company Rhône-Poulenc.

The silicone waxes which can be used in the composition according to the invention include substituted linear polysiloxanes. Mention may be made, for example, of polyether silicone waxes.

The silicone wax can generally be present in an amount of 0–8 weight % in the final composition, preferably in an amount of 2–6%.

The non-silicone fatty substances which can be used in the composition according to the invention include non-silicone oils or mixtures of non-silicone oils, such as vegetable, animal, mineral or synthetic oils or fatty acid triglycerides.

Mention may be made of liquid paraffin, liquid petrolatum, perhydrosqualene, arara oil or sweet almond, calophyllum, palm, castor, avocado, jojoba, olive or cereal germ oil.

It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols, caprylic/capric triglycerides or triglycerides of $C_{10}$ to $C_{18}$ fatty acids. Preferably, the composition of the invention does not contain one or both of sorbitan monoisostearate and diglycerol monoisostearate.

It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

It is also possible to use non-silicone waxes, among which may be mentioned animal waxes, such as beeswax; vegetable waxes, such as carnauba, candelilla, ouricury or japan wax or cork fiber or sugarcane waxes; mineral waxes, for example paraffin or lignite wax or microcrystalline waxes or ozokerites; or synthetic waxes, including polyethylene waxes and the waxes obtained by the Fischer-Tropsch synthesis.

The invention also makes it possible to prepare a cosmetically acceptable composition comprising, in its fatty phase, only cyclic and volatile silicone oils.

As these oils evaporate on contact with the skin, it is thus possible to obtain cosmetic compositions which have no greasy effect, which are particularly valued for skins with a greasy tendency.

The composition can also comprise pigments and/or fillers commonly used in such cosmetic compositions. The pigments can be present in the fatty phase, generally in an amount of 0–15 weight % of the final composition, and preferably in an amount of 1.5 to 12%.

They can be white or colored and inorganic and/or organic and/or pearlescent.

Mention may be made, without implied limitation, of titanium dioxide ($TiO_2$), zinc oxide (ZnO), zirconium dioxide ($ZrO_2$), black, yellow, red or brown iron oxides, cerium dioxide ($CeO_2$), chromium oxide or iron blue, among inorganic pigments.

Among organic pigments, mention may be made of carbon black and barium, strontium, calcium or aluminum lakes.

Among pearlescent pigments, mention may be made of mica covered with titanium oxide or with bismuth oxychloride and of colored titanium oxide-coated mica.

The fillers, which can be present in the proportion of 0–12% of the final composition, can be inorganic or synthetic and lamellar or non-lamellar.

Mention may be made of talc, mica, silica, kaolin, nylon and polyethylene powders, teflon, starch, titanium oxide-coated mica, natural mother-of-pearl, boron nitride, hollow microspheres, such as Expancel from Nobel Industrie, and silicone resin microbeads (Tospearls, for example).

According to whether the final composition is provided in the form of an emulsion, of a paste, which may or may not be anhydrous, of a compound or cast powder or in any other form which can be envisaged in cosmetics, it can comprise the constituents commonly used.

These constituents are preferably chosen according to the cosmetic effect desired for the final composition, such as covering power, transparency, mattness and/or the satiny appearance.

Mention may be made, without implied limitation, of:

gelling agents, such as the modified clays known under the names of bentone, sold by the company NL Industrie and used as is or conditioned beforehand in a gel; hydrophobic silica; waxes, for example polyethylene; aluminum fatty salts; or carboxymethyl cellulose. The percentage of gelling agent in the composition will be chosen according to whether a soft or creamy formula is desired.

vitamins, such as tocopherols and their derivatives, vitamin A and its derivatives, or vitamin C and its derivatives, such as the fatty esters including the palmitate.

sunscreens, such as octyl methoxycinnamate (Parsol MCX), 3-benzophenone (Uvinul M40) or butyl-methoxydibenzoylmethane (Parsol 1789).

oily materials, such as vegetable oils, synthetic esters, lecithin, fragrances or essential oils.

humectants, such as propylene glycol and glycerol.

When the composition is provided in the form of an emulsion, it can also comprise a surface-active agent, for example a conventional anionic or nonionic surface-active agent. The surface-active agent is preferably present, in the aqueous phase, in the proportion of 2–8 weight % of the composition.

The processes for the manufacture of the compositions according to the invention do not differ in any way from the processes conventionally used in cosmetics and fully known to a person skilled in the art.

The compositions according to the invention can be provided in the form of a make-up product for the skin, such as a foundation cream, a tinted or white cream, a lipstick, mascara, a loose make-up powder, a blusher or an eye-shadow.

The invention is illustrated in more detail in the following examples.

EXAMPLE 1

A foundation cream was prepared which had the following composition:

| fatty phase | |
|---|---|
| cyclopentadimethylsiloxane (D5 oil) | 9g |
| cyclohexadimethylsil.oxane (D6 oil) | 7.5g |
| polyether silicone wax | 4g |
| non-volatile silicone oils (polyphenyl-methylsiloxane and polycetylmethyl-siloxane) | 12g |
| mixture of silicone gum and oil (15% polydimethyldiphenylsiloxane in cyclo-pentadimethylsiloxane) | 1g |
| emulsifier | 7.5g |
| pigments | 11g |
| fillers (nylon powder, silicone resin beads) | 3g |
| aqueous phase | |
| magnesium sulfate | 1g |
| glycerol | 2g |
| propylene glycol | 3g |
| polyethylene glycol | 4.7g |
| carboxymethyl cellulose | 0.1g |
| water | q.s. for 100g |

The composition was prepared by heating the constituents of the fatty phase, without the volatile oils, to 65° C. while mixing. The volatile oils were then added at 60° C. The aqueous phase was prepared in parallel by bringing all its constituents to 80° C. while mixing. Cooling was allowed to take place to 30° C.

The two phases were then mixed using a turbine at a speed of approximately 2500 rev/min.

A fluid and colored foundation cream was thus obtained which had a pleasant texture, which spread well and which was uniformly applied.

The make-up obtained was uniform and natural and retained a good hold.

EXAMPLE 2

The amount of volatile silicone oil which evaporated with time was measured for a composition held at 25° C. or 32° C.

As the temperature of 32° C. is a temperature very close to that of the skin, conditions during a skin application were thus approached.

A 3 mg sample of the composition prepared in Example 1 was distributed uniformly over a 3 cm² glass plate which was placed in an oven at the appropriate temperature.

The amount of silicone oil evaporated with time was determined, the following results were obtained:

| | % of oil evaporated at 25° C. | | % of oil evaporated at 32° C. | |
|---|---|---|---|---|
| | D5 oil | D6 oil | D5 oil | D6 oil |
| After 1 min | 16% | 1% | 20% | 2% |
| After 5 min | 62% | 9.5% | 64% | 21.5% |
| After 15 min | 94% | 32% | 95% | 73% |
| After 30 min | 99.5% | 57% | 100% | 98% |
| After 60 min | — | 92% | — | 100% |
| After 120 min | — | 98% | — | — |

The mean application time of a foundation cream was approximately 2 minutes.

It was therefore validly estimated that, during the application of a foundation cream according to the invention, most of the D5 oil (⅔rds) will be evaporated after 5 minutes, the D6 oil remaining on the skin for approximately 30 to 60 minutes.

EXAMPLE 3

The composition of Example 1 was qualitatively compared with two control compositions:

the composition A comprising the D5 oil as the sole volatile oil, the composition B comprising the D6 oil as the sole volatile oil.

The remainder of the constituents of the compositions were identical.

The following results were obtained:

the composition A was less comfortable to use than the composition according to the invention; it was drier and less smooth on spreading.

the composition B was more in evidence on spreading than the composition according to the invention; it was also less evanescent.

EXAMPLE 4

The following foundation cream composition was prepared:

| fatty phase | |
|---|---|
| cyclopentadimethylsiloxane | 4g |
| cyclohexadimethylsiloxane | 10g |
| emulsifier | 3g |
| pigments | 7g |
| fillers | 10g |
| aqueous phase | |
| propylene glycol | 6.5g |
| polyethylene glycol | 10g |
| water | q.s. for 100g |

A foundation cream was thus obtained which was easily applied and which had the specific feature of only containing volatile oils.

Thus, after evaporation of these two oils, make-up was obtained which was free of fatty substances.

What is claimed is:

1. A composition having at least one cosmetic property comprising, in a fatty phase, a combination of volatile cyclic silicone oils comprising from 2–18 weight % of cyclopentadimethylsiloxane and from 2–18 weight % of cyclohexadimethylsiloxane, the weight percentages based on the total weight of the composition.

2. The composition according to claim 1, additionally comprising at least one volatile oil other than said cyclopentadimethylsiloxane and cyclohexadimethylsiloxane.

3. The composition according to claim 2, wherein said at least one other volatile oil is a cyclic or linear silicone oil or an organic oil.

4. The composition according to claim 3, wherein said cyclic or linear silicone oil is cyclotetradimethylsiloxane and wherein said organic oil is a paraffin oil.

5. The composition according to claim 2, wherein the total amount of volatile oils ranges from 4–20 weight % with respect to the total weight of the composition.

6. The composition according to claim 1, additionally comprising a silicone wax.

7. The composition according to claim 6, wherein said silicone wax is present in an amount of up to 8 weight % based on the total weight of the composition.

8. The composition according to claim 1, additionally comprising at least one non-silicone fatty substance, said fatty substance being a vegetable oil, an animal oil, a mineral oil, a synthetic oil, a fatty acid triglyceride, an animal wax, a vegetable wax, a mineral wax, or a synthetic wax.

9. The composition according to claim 1, additionally comprising at least one non-silicone fatty substance, said fatty substance being liquid paraffin, liquid petrolatum, perhydrosqualene, arara oil, sweet almond oil, calophyllum oil, palm oil, castor oil, avocado oil, jojoba oil, olive oil, cereal germ oil, an ester of lanolic acid, of oleic acid, of lauric acid, of stearic acid or of myristic acid, an alcohol, an acetylglyceride, an octanoate, a decanoate or a ricinoleate of an alcohol or of a polyalcohol, a caprylic/capric triglyceride, a triglyceride of $C_{10}$ to $C_{18}$ fatty acids, a hydrogenated oil which is solid at 25° C., a mono-, di-, tri- or sucroglyceride, a lanolin, a fatty ester which is solid at 25° C., beeswax, carnauba wax, candelilla wax, ouricury wax or japan wax, cork fiber or sugarcane wax, paraffin wax, lignite wax, a microcrystalline wax, an ozokerite wax, a polyethylene wax, or a wax obtained by the Fischer-Tropsch synthesis.

10. The composition according to claim 9, wherein said alcohol is oleyl alcohol, linoleyl or linolenyl alcohol, isostearyl alcohol or octyldodecanol.

11. The composition according to claim 9, wherein said hydrogenated oil which is solid at 25° C. is castor oil, palm oil, coconut oil, or tallow oil.

12. The composition according to claim 1, additionally comprising at least one pigment or filler.

13. The composition according to claim 1, wherein said fatty phase contains, as fatty substances, only cyclic and volatile silicone oils.

14. The composition according to claim 13, wherein the only oils in said fatty phase are cyclopentadimethylsiloxane and cyclohexadimethylsiloxane.

15. The composition according to claim 1, which is provided in the form of a make-up product for the skin.

16. The composition according to claim 15, wherein said make-up product is a foundation cream, a tinted or white cream, a lipstick, a mascara, a loose make-up powder, a blusher or an eyeshadow.

17. A method for preparing a cosmetic composition containing a fatty phase, said method comprising the step of including in said fatty phase of said cosmetic composition a combination of volatile cyclic silicone oils comprising from 2–18 weight % of cyclopentadimethylsiloxane and from 2–18 weight % of cyclohexadimethylsiloxane, the weight percentages based on the total weight of the composition.

18. A method for preparing a cosmetic composition, said method comprising the step of preparing a cosmetic composition containing a fatty phase, wherein from 2–18 weight % based on the totol composition of cyclopentadimethylsiloxane and from 2–18 weight % based on the totol composition of cyclohexadimethylsiloxane are included in said fatty phase to provide a cosmetic composition which, after application and evaporation of said cyclopentadimethylsiloxane and cyclohexadimethylsiloxane, is not oily to the touch, and wherein said cyclopentadimethylsiloxane and cyclohexadimethylsiloxane are also included because the rate of evaporation of said cyclohexadimethylsiloxane is slower than that of said cyclopentadimethylsiloxane.

* * * * *